(12) United States Patent
Hayes et al.

(10) Patent No.: US 6,338,715 B1
(45) Date of Patent: Jan. 15, 2002

(54) DIGITAL OLFACTOMETER AND METHOD FOR TESTING OLFACTORY THRESHOLDS

(75) Inventors: Donald J. Hayes, Plano; Ioan Achiriloaie; David W. Taylor, both of Dallas; Norman Comparini, Garland; David B. Wallace, Dallas, all of TX (US)

(73) Assignee: MicroFab Technologies, Inc., Plano, TX (US)

( * ) Notice: Subject to any disclaimer, the term of this patent is extended or adjusted under 35 U.S.C. 154(b) by 0 days.

(21) Appl. No.: 09/540,836

(22) Filed: Mar. 31, 2000

Related U.S. Application Data

(60) Provisional application No. 60/127,079, filed on Mar. 31, 1999.

(51) Int. Cl.[7] .................................................. A61B 5/08
(52) U.S. Cl. ...................................... 600/303; 73/23.34
(58) Field of Search .......................... 600/303; 73/23.34

(56) References Cited

U.S. PATENT DOCUMENTS

| | | | |
|---|---|---|---|
| 3,885,550 A | * 5/1975 | MacLeod | ..................... 600/303 |
| 4,265,248 A | * 5/1981 | Chuiton et al. | ............. 600/303 |
| 4,911,892 A | 3/1990 | Grace et al. | |
| 5,053,100 A | 10/1991 | Hayes et al. | |
| 5,145,645 A | 9/1992 | Zakin et al. | |
| 5,177,994 A | 1/1993 | Moriizumi et al. | |
| 5,284,133 A | 2/1994 | Burns et al. | |
| 5,461,403 A | 10/1995 | Wallace et al. | |
| 5,511,726 A | 4/1996 | Greenspan et al. | |
| 5,565,148 A | 10/1996 | Pendergrass Jr. | |
| 5,591,409 A | 1/1997 | Watkins | |
| 5,658,802 A | 8/1997 | Hayes et al. | |
| 5,681,757 A | 10/1997 | Hayes et al. | |
| 5,756,879 A | 5/1998 | Yamagishi et al. | |
| 5,777,207 A | 7/1998 | Yun et al. | |
| 5,801,297 A | 9/1998 | Mifsud et al. | |
| 5,894,841 A | 4/1999 | Voges | |
| 5,904,916 A | 5/1999 | Hirsch | |
| 6,006,583 A | * 12/1999 | Hayashi | .................. 600/303 X |

FOREIGN PATENT DOCUMENTS

| | | |
|---|---|---|
| AU | 70632/94 | 6/1994 |
| EP | 0432992 A1 | 6/1991 |
| EP | 0542723 A2 | 5/1993 |
| GB | 2272389 | 5/1994 |
| WO | WO 92/11050 | 7/1992 |
| WO | WO 93/10910 | 6/1993 |

OTHER PUBLICATIONS

U.S. application No. 08/837,646 Hayes et al.
U.S. application No. 08/837,646 pending.
U.S. application No. 09/110,486 Hayes et al.
U.S. application No. 09/110,486 pending.
U.S. application No. 09/176,818 Frederickson et al.
U.S. application No. 09/176,818 pending.

* cited by examiner

*Primary Examiner*—Eric F. Winakur
*Assistant Examiner*—Ryan Carter
(74) *Attorney, Agent, or Firm*—Locke Liddell & Sapp LLP

(57) ABSTRACT

A more reliable and precise method of determining the olfactory threshold is provided by a digitally operated apparatus that dispenses controlled amounts of a volatile test fluid from a digital jetting device of the type used for ink jet printing. A precise number and size of micro droplets are dispensed onto a heater which vaporizes the fluid at a test location where a patient can sniff and report whether the odor is sensed. Incremental adjustments are made to determine the approximate threshold of olfactory perception of the odor. Sensors are included to verify dispensing and to coordinate dispensing with breathing.

10 Claims, 5 Drawing Sheets

Disposable Unit

Vapor Sensor

DIGITAL OLFACTOMETER AND METHOD FOR TESTING OLFACTORY THRESHOLDS

CROSS REFERENCE TO RELATED APPLICATIONS

This is a continuation of U.S. patent application Ser. No. 60/127,079 filed Mar. 31, 1999 entitled as above for which benefit under 35 U.S.C. § 119(e) is claimed.

BACKGROUND OF THE INVENTION

1. Field of the Invention

The invention discloses an apparatus and method for measuring olfactory threshold.

2. Background of the Art

The measurement of olfactory thresholds are beneficial in evaluating and managing a number of human conditions. Some of these are: damage to the olfactory nerves or olfactory bulb by head trauma; early detection of Alzheimer disease and Parkinson's disease; damage due to acute viral and/or bacterial infections, e.g. HIV; damage to the olfactory system due to exposure to fumes and chemicals; side-effects from radiation therapy to the head; and others. A medical diagnostic instrument that can measure olfactory thresholds in an accurate mainer, quickly and at a lower cost is needed. This type of instrument could be used not only as a one time evaluation of a patient, but it could be used to trace a patient's progress over time to monitor for onset of a particular occurrence.

The measurement of olfactory thresholds is accomplished today by various means. One method is by using scratch-and-sniff pads where the test operator scratches the surface to expose the odor, puts it up to the patient's nose, and asks for a response. Different parts of the pad expose stronger and stronger odors. Another test method is using squeeze-bottle smell test kits. Here a series of bottles with increasing concentration of vapors is used. In both these methods the freshness of the samples and the skill of the test operator are critical factors in the test results. Obtaining good quantitative test results is difficult with these methods. Another method is the use of a large research-type olfactometer. The disadvantage to this method is that the test is slow and the cost of the instrument is very high. The present invention overcomes the disadvantages of the present methods.

SUMMARY OF THE INVENTION

The instrument described in this patent application was initially focused on Alzheimer and Parkinson disease, but can be applied to all of the above conditions and others that have similar degenerative effects on the region of the brain that controls olfactory response. The key component of the instrument is a jetting device that dispenses small, precise, known quantities of the odor causing fluid onto a heated surface which causes fluid to be vaporized and transported to the patient under test. Patent applications "Method and Apparatus for Delivery of Fragrances and Vapors to the Nose", Ser. No. 09/176,818 filed Oct. 22, 1998 and "Presenting Airborne Material to the Nose", application Ser. No. 08/837,646 filed Apr. 21, 1997 are incorporated herein by reference.

The concentration of vapor molecules exposed to the nose of the person being tested is dependent on the number and size of the droplets deposited onto the heater surface. By varying the number of droplets and evaluating whether or not the patient smells the odor, the threshold can be determined accurately. Because the concentration of the vapor exposed to the nose is digitally controlled, the entire testing process can be run either automatically or under the control of a test operator. Sensors can be incorporated into the instrument to measure concentration of the vapors directly, to measure when the patient has sniffed, and the exact number of droplets dispensed. Each of these sensors improves the reliability of the testing and therefore can reduce the total test time required. These sensors also allow for self calibration of the instrument and a more operator independent test process.

DETAILED DESCRIPTION OF THE INVENTION

Figure 1:
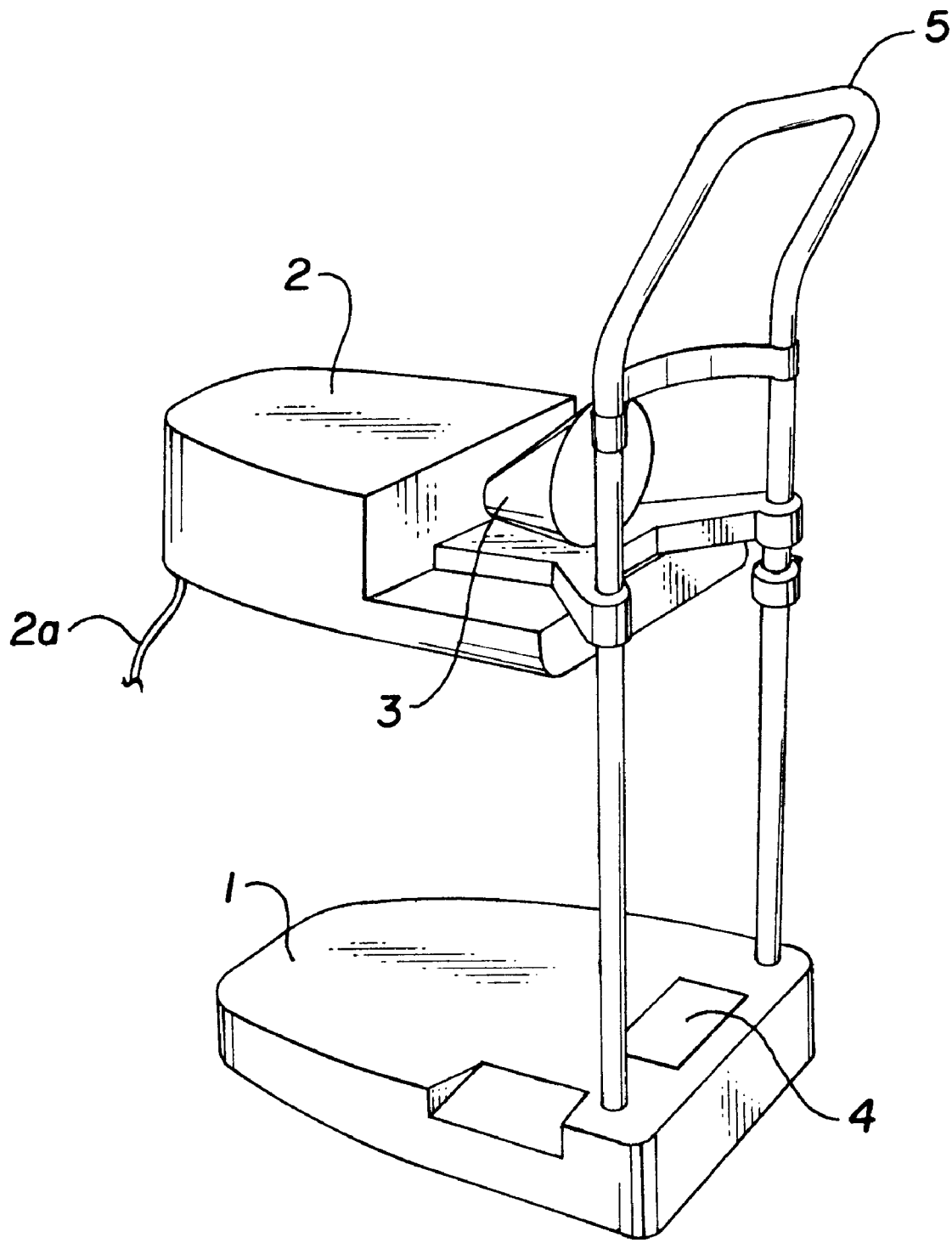
FIG. 1 is a pictorial view of a digital olfactometer instrument designed to establish a reproducible "test location" for patients.

FIG. 1 illustrates a table top olfactometer instrument. It includes a base support 1 and frame 5. The housing for the working part 2 of the instrument contains the jetting device, heater, fan and several sensors. Power supply 2a provides power to working part 2. It can also contain all or part of the electronics and controls. Airway walls 3 constrain the airflow toward the patient's nose. The patient would sit in front of the instrument and place their chin on the chin support 4. The base, support and chin rest is similar to medical diagnostic instruments for eye testing.

Figure 2:
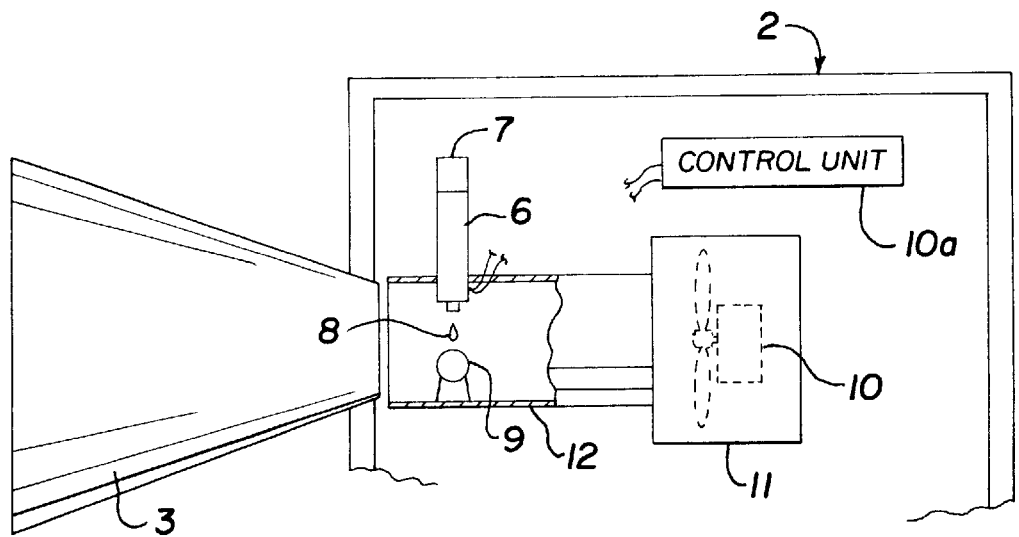
FIG. 2 is a schematic side elevational view of the dispensing portion of the olfactometer of FIG. 1.

FIG. 2 shows the components that are inside housing 2. The jetting device 6 dispenses droplets of fluid 8 onto the heater 9 where the fluid is transformed into vapor. The heater temperature is set to a temperature required to evaporate the fluid jetted onto it in a reasonable time. The wetting conditions of the heater surface and the surface roughness is a parameter to be determined. A fluid reservoir 7 is connected to the jetting device and supplies the fluid to be dispensed to the jetting device. In the preferred embodiment the fluid to be jetted is phenylethyl alcohol, although many other fluids that give off an odor could be used. A fan 10 is used to supply a low flow of air to carry the vapors coming off the heater surface to the patient's nose through the airway walls 3. The fan is housed in a case 11 which is mounted into the housing. A structural tube 12 carries the air from the fan to the heater to the airway passages. This tube can also contain the mounting for the heater and the jetting device. A control unit 10a is operably connected to jetting device 6 to drive and control output. It may have a programmed microprocessor to operate the drive electronics or even a switch or push button that allows the operator to manually control dispensing. The control and drive electronics for ink jet type jetting devices are well known in the art.

Apparatus with minimal surface area heaters are preferred because they produce minimal heating of the delivered air, thus creating minimal distraction or confusion for the subject. Another characteristic of heaters for this invention is that they do not produce an odor when heated. This is both critical and difficult to achieve. In addition, the target surface of a heater must allow wetting so that droplets do not bounce off the surface but wet it instead. A ceramic cement which wetted well, had no odor of its own after a little burn in time and withstood the heat is available through Cotronics Corp., Brooklyn, N.Y. identified as Durapot 801 is rated to 1650° C. The cement desirably enhances surface roughness of the heater which greatly improves wettability. It is also contemplated that surface roughness to improve wetting could be provided to the heating surface of the heater (impact surface) by such means as sand blasting, wire brush, sanding, ablation or other forms of abrasion.

Two types of heaters that worked well are surface mount resistors and thin film devices including platinum resistance temperature devices (RTD's). Surface mount resistors are rugged, inexpensive and readily available in a wide range of resistance values. Experimentation will readily determine the best resistance value for a particular temperature. If temperature control is desired, the RTD's are preferred. They are available through Omega Engineering, Stamford, Conn. as part number TFD. Any of their thin film devices are useable. TFD's which had a resistance of 100 ohms and range of 100 volts D.C. were operated around 24 volts. Using RTD's at temperatures above the melting point of solder is possible as the leads are attached to allow temperature of 550° C. The temperature to evaporate phenylethyl alcohol, for instance was around 240° C. This is known to be a useful solvent for fragrance dispensing. Other volatile fluids may be used as well.

Figure 3:
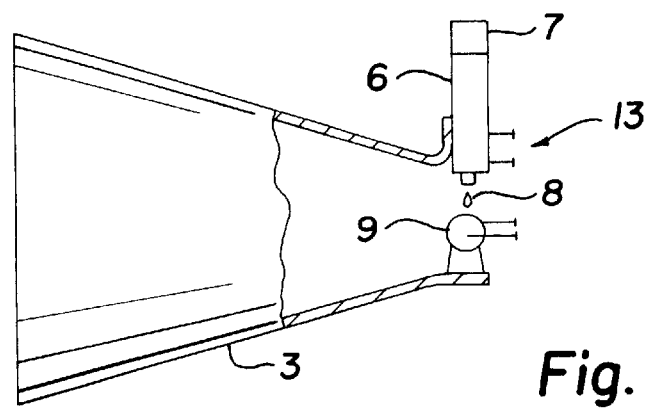
FIG. 3 is a schematic side elevational view of a disposable part of a digitally operated olfactometer like FIG. 1.

In the medical field, disposable (consumable) devices are common for sanitary reasons. FIG. 3 illustrates a disposable design. The digital olfactometer would have a disposable part and a supporting part. The supporting part might be the housing, fan case and tube part with electrical connections or plug in connections for power and control for the disposable part. In this embodiment the disposable part or unit would contain the jetting device 6 with reservoir 7 supplying fluid to the jetting device and electrical connections 13 which could automatically snap into position as the disposable part is installed into the instrument. The heater 9 could be included with the disposable unit, attached to the airway walls 3. FIG. 3 shows the consumable part all connected together as a single disposable component. A sub-set of this combination is also possible. In another embodiment only the airway 3 that is close to the patient might be disposable.

Various types of vapor sensors can be used in monitoring and calibrating the olfactometer instrument. Some electronic chemical sensors, are discussed in U.S. patent application Ser. No. 08/837,646 and 09/176,818 which have been incorporated by reference and are also believed known to one of ordinary skill in the art. Electronic noses are discussed in some detail in the following references which are incorporated herein by reference. Baletz, Lange, and Koll, "The Electronic Nose in Lilliput", IEEE Spectrum, pp. 36–38, September 1998 and Kaplan and Braham, "The How and Why of Electronic Noses", IEEE Spectrum, pp. 22–34, September 1998. The former of these mentions an experimental electronic nose that could easily fit in a wristwatch. The invention provides a means for real time calibration of electronic chemical sensor arrays used in electronic noses which are capable of analyzing complex odors and vapors. Electronic noses work by comparing process signals from a sensor array with known patterns stored in a data base.

Various types of sensor arrays which are possible include conductive polymer sensors (U.S. Pat. Nos. 5,801,297; 5,145,645; 4,911,892; and 5,756,879), metal oxide conductivity sensors (U.S. Pat. No. 5,777,207), quartz resonator type sensors (U.S. Pat. No. 5,177,994), polymerdielectric sensor (capacitor), fluorescent optical sensor, etc. The type of sensor will determine the key features: number of sensor elements, detector sensitivity (threshold and response curve), stability, reproducibility, response time and refresh time. The above mentioned U.S. patent are incorporated herein by reference.

Figure 4:
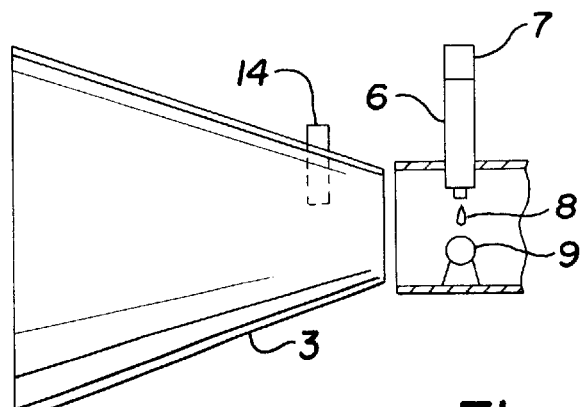
FIG. 4 is a schematic side elevational view of an alternate embodiment of the olfactometer of any of the previous Figures in which a vapor sensor in the airway can be used to monitor output of the droplet jetting device in the olfactometer.

FIG. 4 illustrates one location where the vapor sensor 14 might be located. It's location would be determined by the definition of the consumable. The vapor sensor would not normally be part of the consumable. The vapor sensor would measure the concentration of the vapor at a specific location.

Figure 5:
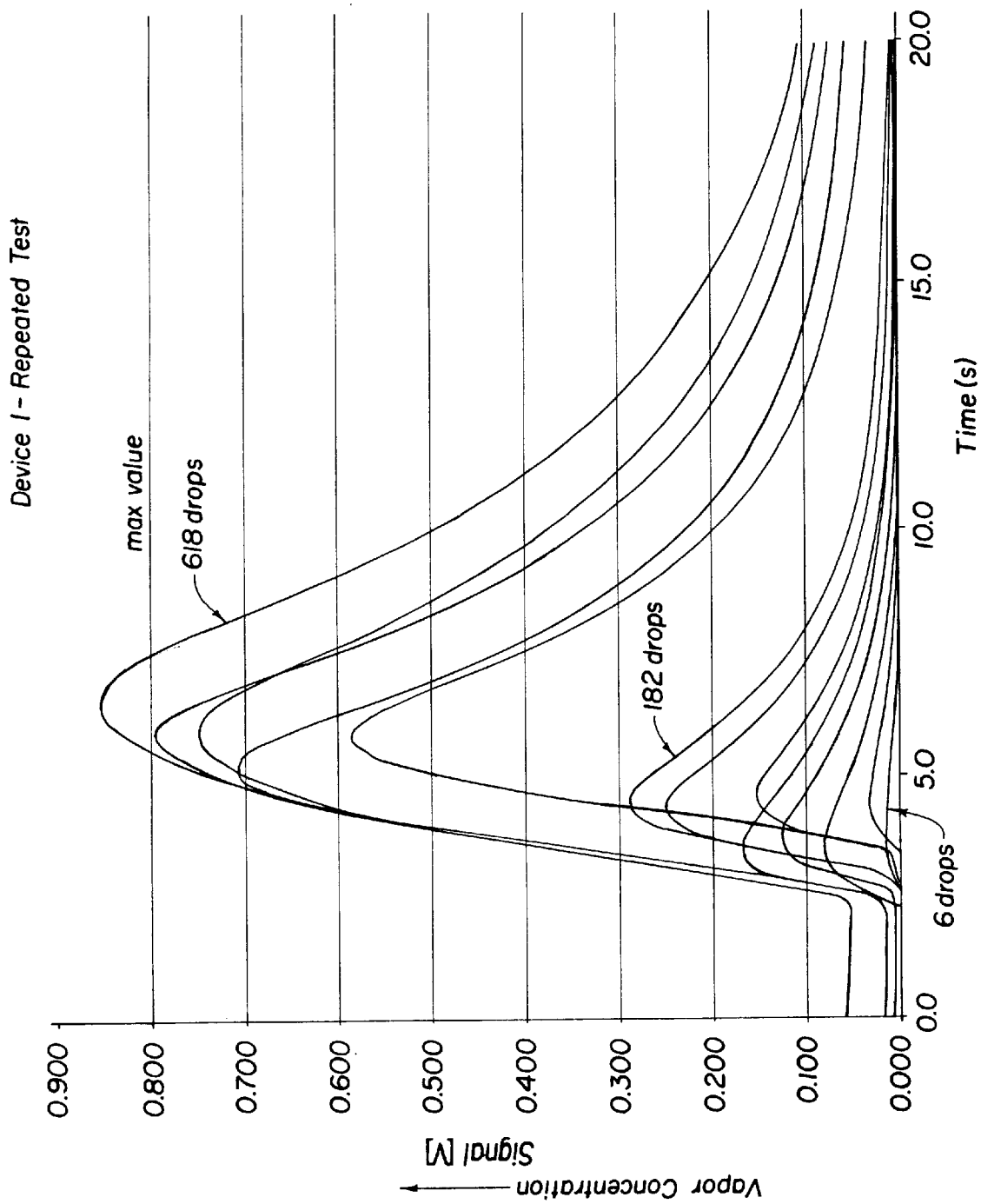
FIG. 5 represents sample data taken during use of the vapor sensor embodiment of FIG. 4 showing that even a small number of drops can be monitored as a measure of vapor concentration.

FIG. 5 shows the data from such a vapor sensor. These data show the concentration of vapor molecules at the sensor as a function of time. It can be seen from this data that concentration increases with the number of drops. It is also seen that a measure of vapor concentration (signal) is easily noticed even at a relatively small number of drops of dispensed volatile fluid. In the preferred embodiment, this sensor is used to calibrate the system so that the correct concentration is presented to the patient. This sensor would be used to calibrate the system each time a new consumable is installed into the system, especially if the consumable includes any of the following: the jetting device, reservoir of fluid, or the heater. In one embodiment, the system would automatically calibrate each time a new component was installed.

It could also self-calibrate before each new test or on command. The sensor signal could be caused to actuate a visual or audible signaling device to show that the vapor was or was not present at the test location when a dispensing step was performed.

Figure 6:
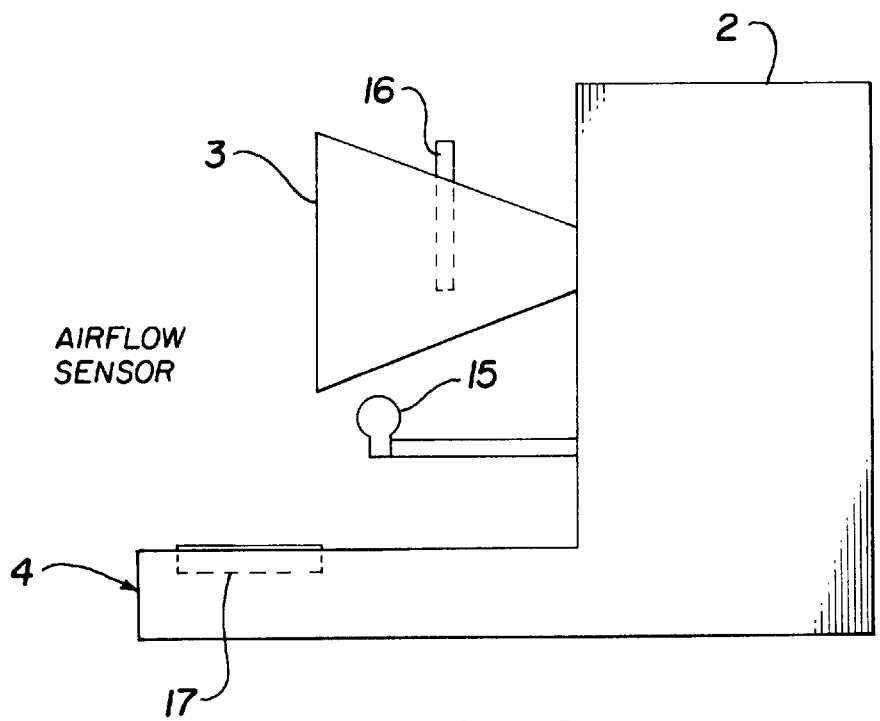
FIG. 6 is a schematic side elevational view of a digital olfactometer of the invention showing several ways in which "airflow" or a measure of airflow can be detected and used to initiate the dispensing of droplets by the digital olfactometer.

FIG. 6 illustrates a sniff sensor. It is important in running the test to insure that the patient sniffs or breathes when the vapor is present. Various types of sniff sensors are possible: a microphone 15, a hot wire anemometer 16, a pressure/acoustic sensor 17 mounted in the chin support. The sniff sensor is used to verify that the sniff occurred when the vapor is present. It helps coordinate the sniff with jetting. In the manual mode, it is an aid to the test operator. In the automatic mode, it would coordinate the test and repeat a particular test if the correlation was off. In one case it helps the operator make a decision about the timing of the two events (sniffing and jetting). In the other case it is done fully automatically by the system controller. In the preferred embodiment, the microphone is the type of sensor proposed.

Figure 7:
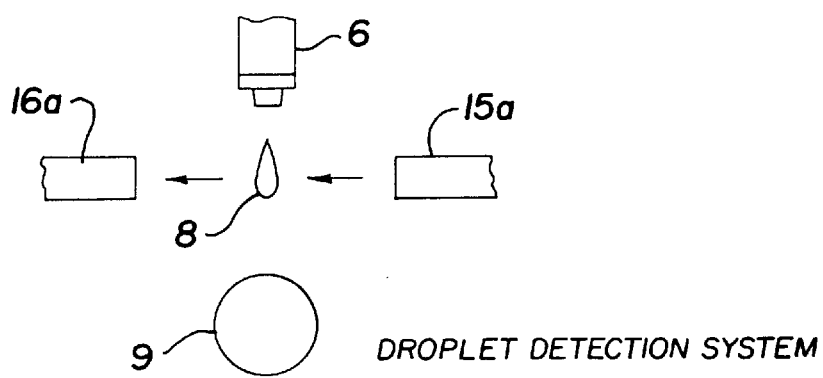
FIG. 7 is a schematic side elevation of an embodiment of the digital olfactometer of the invention equipped with a droplet detection device which can be used to make sure droplets are being emitted.

FIG. 7 shows a droplet detection system. It consists of a light source (LED) 15a which shines a light onto a detector 16a which receives a signal. When a droplet 8 passes in front of the detector it blocks a part of the light and reduction in the signal is detected. Each time a droplet passes this event happens. If the olfactometer is programmed it dispense 40 droplets, 40 signals should be detected and counted. The electronics for counting and reporting is standard and certainly known to one skilled in the art. The type of droplet detection system would be used to verify that the number of drops programmed to be ejected were actually jetted. This system adds another level of reliability to the overall test.

Figures 8, 8A:
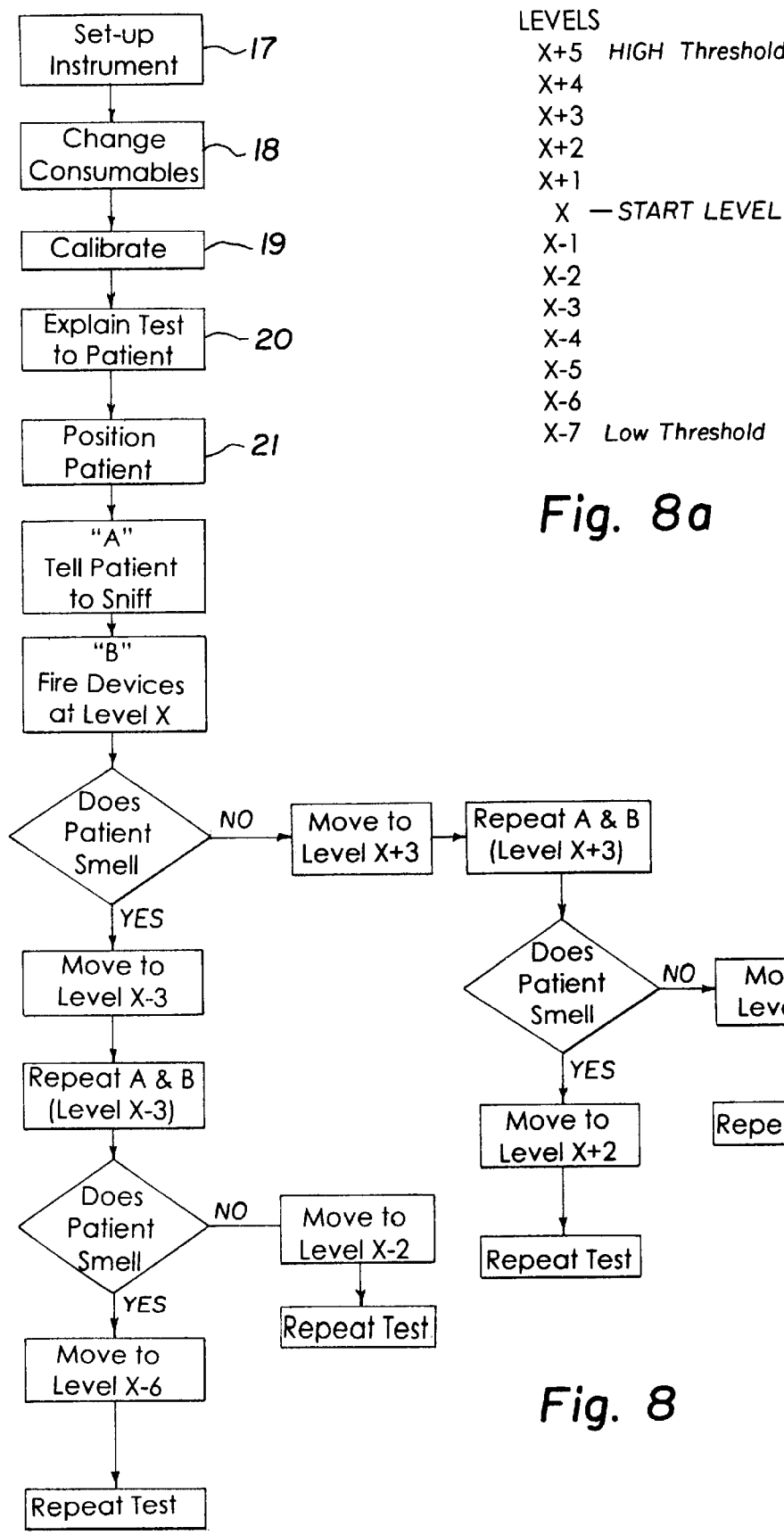
FIG. 8a is a threshold level chart which illustrates numerically incremental changes in the amount of material dispensed for a test from an arbitrary starting level X.
FIG. 8 represents a flow chart of steps involved in use of the digital olfactometer of the invention to determine the olfactory threshold of a patient.

FIG. 8 illustrates how a typical olfactory threshold test would be run. The goal of the test is to identify the minimum concentration level that a person could detect. Above this level they would identify the presence of an odor and below this level they could not detect the odor. Steps 17, 18, 19, 20 and 21 are events that prepare for the actual testing. These include setting up the instrument, changing consumables, calibration, explaining the test to the patient, and positioning the test (Level X). Level X might be somewhere around what is believed to be a typical olfactory threshold level for a person of normal characteristics. Level X corresponds to a certain vapor concentration level. If the patient detects the odor at this level then the concentration is lowered by 3 levels and the test is repeated. If the patient does not detect level X that the level is raised by 3 levels and the test repeated. This process is continued until the threshold level is defined. Once defined the test would be repeated for verification. It should be obvious to one skilled in the art that variations and modifications of this process are possible with the same overall goal reached. FIG. 8a illustrates a scale that shows X–7 is a good sensitivity level (low olfactory threshold) and that X+5 is a poor sensitivity level (high olfactory threshold).

The type of system described in this, patent application can be used to measure the Trigeminal Response to irritations. In this case different fluids would be used and may require higher vapor concentrations. For a particular odor the olfactory threshold to smell and the trigeminal threshold could both be measured.

What is claimed:

1. A method of determining a patient's olfactory threshold, comprising the steps of:
   a.) providing a digitally controlled and operated olfactometer comprising a jetting device capable of dispensing controlled amounts of volatile fluid at a test location;
   b.) placing a patient's nose at the test location;
   c.) dispensing a controlled amount of volatile fluid from the jetting device and converting the fluid to vapor at the test location;
   d.) determining if the patient has or has not sensed the volatile fluid vapor at the test location;
   e.) dispensing respectively an increased incremental known quantity of volatile fluid if the patient has not sensed the volatile fluid vapor or a reduced incremental known quantity of volatile fluid if the patient has sensed the volatile fluid vapor;
   f.) repeating steps c–e respectively at incremental higher or lower known volatile fluid vapor concentrations until the patient no longer senses the volatile fluid vapor if the patient was sensing it or senses the volatile fluid vapor if the patient was not sensing it; and
   g.) wherein the patient's olfactory threshold is determined by determining a measure of the concentration in effect at the time a change in the patient's state of sensing the volatile fluid vapor was detected.

2. The method of claim 1 wherein the olfactometer comprises a non-disposable supporting part and a disposable part containing the jetting device, and the method includes the step of mounting the disposable part in operative combination with the non-disposable supporting part before a dispensing step is initiated.

3. The method of claim 1 wherein a sniff sensor incorporated operably into the olfactometer generates a signal responsive to patient breathing and dispensing steps c.) and e.) are initiated in response to the signal generated by the sniff sensor.

4. The method of claim 3 wherein the sniff sensor is a microphone placed at the test location and the steps of initiating dispensing steps c.) and e.) in response to a signal are performed in response to an output signal generated by the microphone.

5. The method of claim 3 wherein the sniff sensor is a hot wire anemometer placed at the test location and the steps of initiating dispensing steps c.) and e.) in response to a signal are performed in response to an output signal generated by the hot wire anemometer.

6. The method of claim 3 wherein the sniff sensor is a pressure sensor placed at the test location and the steps of initiating dispensing steps c.) and e.) in response to a signal are performed in response to an output signal generated by the pressure sensor.

7. The method of claim 1 wherein a vapor sensor incorporated operably into the olfactometer generates a signal representative of a vapor concentration at the test location when a dispensing step is performed and the method includes the step of using the signal as an indication that said dispensing step was performed.

8. The method of claim 3 wherein a vapor sensor incorporated operably into the olfactometer generates a signal representative of a vapor concentration at the test location when a dispensing step is performed and the method includes the step of using the signal as an indication that said dispensing step was performed.

9. The method of claim 1 wherein a droplet detection system incorporated operably into the olfactometer generates a signal representative volatile fluid droplets being generated by the jetting device at the test location when a dispensing step is performed and the method includes the step of using the signal representative of volatile fluid droplet generation to assure that a given dispensing step was or was not performed.

10. The method of claim 3 wherein a droplet detection system incorporated operably into the olfactometer generates a signal representative volatile fluid droplets being generated by the jetting device at the test location when a dispensing step is performed and the method includes the step of using the signal representative of volatile fluid droplet generation to assure that a given dispensing step was or was not performed.

* * * * *